United States Patent [19]
Paul et al.

[11] 4,151,209
[45] Apr. 24, 1979

[54] REDUCTION OF CATALYST DEACTIVATION IN PROCESSES FOR HYDROFORMYLATION OF OLEFINS WITH RHODIUM COMPLEX CATALYSTS

[75] Inventors: James L. Paul; Wendell L. Pieper; Leslie E. Wade, all of Corpus Christi, Tex.

[73] Assignee: Celanese Corporation, New York, N.Y.

[21] Appl. No.: 846,296

[22] Filed: Oct. 28, 1977

Related U.S. Application Data

[63] Continuation of Ser. No. 685,836, May 13, 1976, abandoned.

[51] Int. Cl.$^2$ .............................................. C07C 45/08
[52] U.S. Cl. ............................................ 260/604 HF
[58] Field of Search ................................. 260/604 HF

[56] References Cited

U.S. PATENT DOCUMENTS

| | | | |
|---|---|---|---|
| 3,239,566 | 3/1966 | Slaugh et al. | 260/604 HF |
| 3,821,311 | 6/1974 | Hughes | 260/604 HF |

FOREIGN PATENT DOCUMENTS

| | | | |
|---|---|---|---|
| 2062703 | 7/1970 | Fed. Rep. of Germany | 260/604 HF |
| 1298331 | 11/1969 | United Kingdom | 260/604 HF |

*Primary Examiner*—Werren B. Lone
*Attorney, Agent, or Firm*—Ralph M. Pritchett

[57] ABSTRACT

In a process for hydroformylating an olefin in the presence of a catalyst comprising rhodium in complex combination with carbon monoxide and a triorganophosphorus ligand, progressive deactivation of the catalyst, as well as loss of the ligand species through by-product formation, are reduced by continuously stripping the liquid reaction medium to a degree such that the content of high-boiling organophosphorus by-products therein is maintained at a low level such that the ratio of phosphorus contained in said high-boiling by-products to phosphorus contained in the ligand present in the reaction medium does not exceed about 0.2.

11 Claims, No Drawings

REDUCTION OF CATALYST DEACTIVATION IN PROCESSES FOR HYDROFORMYLATION OF OLEFINS WITH RHODIUM COMPLEX CATALYSTS

This is a continuation, of application Ser. No. 685,836, filed May 13, 1976, abandoned.

BACKGROUND OF THE INVENTION

Processes for hydroformylating an olefin to prepare a carbonyl derivative containing one carbon atom more than the parent olefin by reacting the olefin with synthesis gas in the presence of a rhodium catalyst in complex combination with carbon monoxide and a triorganophosphorus ligand (e.g., triphenylphosphine) are well known in the art and of growing industrial importance. This technology is summarized, for example, in U.S. Pat. No. 3,527,809 issued Sept. 8, 1970 to Pruett et al. The olefin reactant, together with a gaseous mixture of carbon monoxide and hydrogen, is typically bubbled through a liquid reaction medium, which may or may not comprise a separate inert liquid solvent species, which contains as hydroformylation catalyst a complex of rhodium with carbon monoxide and a triorganophosphorus ligand, the ligand typically being present in some excess. It will be understood also that hydrogen will be present in the complex during a portion of the catalytic cycle. The carbonyl reaction product is removed from the reaction medium, either by being stripped directly out of the reaction zone in the stream of unreacted synthesis gas exiting from the reaction zone or else by being distilled out of a liquid draw-off stream which is continuously withdrawn from the reaction zone for product recovery. Both techniques may be employed simultaneously, of course.

It is known that some deactivation of the rhodium-containing catalyst takes place with the passage of time, necessitating periodic withdrawal of at least a portion of the liquid contents of the reaction zone for recovery of deactivated rhodium catalyst and reconversion into an active form. This deactivation is, in these systems, a more than ordinarily significant cost factor inasmuch as rhodium, even in very small quantities, is expensive. It is therefore recognized in the art that preventing or minimizing deactivation of the catalyst is of unusual importance in these rhodium-catalyzed reactions.

It is also recognized in the art that there are certain reaction by-products which have an adverse effect on the rhodium catalyst. Specifically, it is taught in German Offenlegungsschrift No. 2062703 that a dimeric unsaturated aldehyde which is a by-product in producing butyraldehyde from propylene has an adverse effect on the rhodium catalyst if its concentration is allowed to build up to levels greater than about five weight percent in the liquid reaction medium. Otherwise, however, the same reference teaches that other high molecular weight by-products (in particular hydroxylic compounds) not only are not deleterious but in fact are very desirable as reaction solvents in the process. Similar teachings appear in British Pat. No. 1298331, which broadly recommends using the entirety of the reaction by-products as reaction solvent without ascribing deleterious properties to any of the components thereof.

Aside from the limited teachings regarding the desirability of avoiding an unlimited buildup of the unsaturated aldehyde by-products discussed above as they relate to deactivation of the rhodium catalyst, the existing prior art is largely silent on the somewhat-related matter of the loss of the triorganophosphorus ligand (e.g., triphenylphosphine) due to chemical combination with various other components of the reaction system. Yet loss of the ligand through, for example, the formation of inert high-boiling polymeric derivatives thereof, is in itself a significant cost item in the hydroformylation processes under consideration even though unit cost of the ligand species is very much lower than that of rhodium.

It is, accordingly, an object of the present invention to provide a method for reducing the rate at which the rhodium catalyst complex is deactivated during the course of the reaction of an olefin, carbon monoxide, and hydrogen in the presence of a catalyst comprising rhodium in complex combination with carbon monoxide and a triorganophosphorus ligand. It is another object to provide a method for reducing losses of the triorganophosphorus ligand due to formation of phosphorus-containing by-products during the course of the same hydroformylation reaction. It is a specific object to provide a method for reducing said catalyst deactivation and said loss of triorganophosphorus ligand in a process for converting an alkene to a carbonyl derivative thereof in the presence of a catalyst consisting essentially of rhodium in complex combination with carbon monoxide and triphenylphosphine. Other objects will be apparent from the following detailed description.

SUMMARY OF THE INVENTION

It has now been discovered that, even though the concentration of unsaturated aldehydic by-products in the reaction medium may be extremely low as compared with the range of 5% or less as discussed in the previously-described prior art, and even if it be, in fact, so low as to be not readily detectable, there is still a progressive deactivation of the rhodium catalyst which is a significant processing cost element even though the deactivation may sometimes be at a rate so low as to be apparent only on a time scale of weeks as compared with, for example, days. It has been discovered furthermore that loss of triorganophosphorus ligand (e.g. triphenylphosphine) from the system by chemical degradation also takes place to a significant extent under conditions previously considered by the art to be normal and entailing no deleterious effects.

It has further been discovered that these above-summarized deleterious effects can be greatly and unexpectedly ameliorated by carrying out the hydroformylation reaction in a manner which comprises continuously stripping the liquid reaction medium, during the course of the reaction, to a degree which is much more intense than that which has heretofore been regarded as adequate. That is, as distinguished from simply stripping to a degree such that the content of unsaturated aldehyde reaction by-products does not exceed about 5 weight percent, the present invention comprises stripping to a degree such that the concentration of all high-boiling organophosphorus reaction by-products, defined as being those organophosphorus by-products which are less volatile than the triorganophosphorus ligand being employed in the process, excluding the oxide of the ligand or a phosphorus containing added inert solvent, is maintained at a level not exceeding that at which the ratio of the phosphorus contained in said high-boiling organophosphorus compounds to the phosphorus contained in the ligand which is present does not exceed about 0.2. The resulting concentration of the unsaturated aldehydes, previously identified in the art as being deleterious, can be so low that they will be, for all practical purposes, entirely absent in the case of butyraldehyde production systems so that the control of the unsaturated aldehydes is not, per se, a significant factor at all inasmuch as the invention contemplates an intensive stripping which is of a much higher order than that which is required simply to avoid high concentrations of these aldehydes (i.e. higher than 5% unsaturated aldehydes).

It is to be pointed out especially that, by the employment of the present improvement, one is not merely removing catalyst poisons and ligand-abstracting chemical moieties. Rather, it has been discovered that this intensive stripping actually results in preventing the formation of catalyst poisons and ligand-abstracting species. The result of applying the present process improvement is both an increase in the effective life of the rhodium component of the catalyst and, in addition, a significant diminution in consumption of the ligand through formation of organophosphorus by-products. It will be understood that the high stripping tends to increase loss of ligand through vaporization, but this is readily controlled by rectifying the evolved vapors and refluxing the recovered ligand back into the reaction zone.

It is believed that the mechanism involved entails preventing or reducing the formation of intermediate reaction condensation products of, for example, the product aldehyde with other organic components of the system. It is also believed that, in the absence of the intensive stripping herein contemplated, there are formed in the reaction certain high molecular weight derivatives of the ligand, the presence of which is correlatable with rhodium deactivation and which attain an unacceptably high concentration in the reaction medium. With the present heavy stripping being employed, these high molecular weight compounds, including the high molecular weight phosphorus-containing by-products, never have a chance to attain a deleterious concentration level.

It will be understood that the foregoing remarks concerning the mechanisms by which the present process is believed to operate are offered only as a provisional explanation in accordance with the best understanding of the phenomenon here involved which are currently available. They are not to be taken as limitations of the scope of the invention nor as precluding alternative explanations.

DETAILED DESCRIPTION AND PREFERRED EMBODIMENTS

The catalyst deactivation phenomenon and the ligand degradation problem with which the present process improvement is concerned occur generally in all processes wherein an alpha-olefin, most commonly an alpha-alkene, is hydroformylated with carbon monoxide and hydrogen in a liquid reaction medium containing a catalytic complex of rhodium with a triorganophosphorus ligand and carbon monoxide to produce a carbonyl derivative of the feedstock olefin. Regardless of the nature of the olefinic feedstock, and regardless of the exact identity of the organophosphorus ligand, the aldehydic moieties and the organophosphorus ligand moieties which are present in all cases are generally susceptible to reactions in which complex by-products of a highly non-volatile nature are ultimately formed unless steps are taken to prevent or reverse these reactions. The presence of these by-products has been found to be associated with rhodium deactivation, by mechanisms which probably entail the formation of complex organ-rhodium or organophosphorus-rhodium compounds which have little or no catalytic activity for the hydroformylation process. Likewise, while not necessarily involving the rhodium as a factor in all cases, these side-reaction processes also entail the formation of catalytically useless high-boiling organophosphorus compounds formed from the ligand whereby there results an uneconomic destruction of the ligand as well as an undesired contamination of the liquid reaction medium.

A significant aspect of the invention is the discovery that simply maintaining at a low level the concentration of the unsaturated aldehydes which are a recognized by-product and which are also considered to be deleterious does not, in itself, solve the problem of catalyst deactivation although it may be a desirable step in this direction. For example, it has been found that, when hydroformylating propylene to product butyraldehyde using triphenylphosphine as the ligand, a progressive deactivation of the rhodium catalyst still took place at a rate high enough to be a serious economic drawback even when the concentration of the eight carbon-atom unsaturated aldehyde recognized in the prior art as being undesirable in this reaction system was so low (i.e., about 0.3%) as to be not reliably detected. Further observation of the same reaction system indicated that a much more serious problem lies in the formation of very high molecular weight reaction by-products, some of which at least contain chemically-bound phosphorus, which are formed by reactions which are believed to be only slowly reversible but which can be kept out of the reaction medium if it is continuously stripped during the course of the reaction to a very much higher degree than heretofore contemplated. That is, these compounds, once formed, are formed in a manner which is only slowly reversible and, being of very high molecular weight or at least of extremely low volatility, cannot easily be removed once they are formed. However, it has also been discovered that the buildup of these compounds to an unacceptably deleterious level can be prevented by using a high degree of stripping. The degree of stripping which has been found to be necessary, or at least very highly desirable, for this purpose is such that the unsaturated aldehydes of moderate molecular weight, known to the prior art to be undesirable by-products, are sometimes almost entirely absent. That is, their concentration may be so extremely low that the upper limit of about 5 weight percent taught by the prior art as being desirable insofar as they are concerned becomes for all practical purposes meaningless. This is especially the case when relatively volatile aldehydes, such as butyraldehyde, are being synthesized.

The high molecular weight phosphorus-containing by-products referred to above, which can be referred to as high molecular weight derivatives of the triorganophosphorus ligand although their exact composition is not known, are of such low volatility that they are even less volatile than triphenylphosphine oxide, which may in certain cases be a desirable component of the liquid reaction medium as will be further discussed hereinbelow. If the liquid reaction medium is one which, throughout its entire life in the reaction zone, has been continuously employed under conditions of high stripping as will be further defined hereinbelow, these refractory compounds do not build up to an unacceptably deleterious level and the catalyst deactivation rate is greatly reduced.

It is believed, although other explanations are possible and the present disclosure is not to be interpreted solely in accordance with this mechanistic theory, that the concentration of the product aldehyde in the reaction zone, as well as its residence time therein, may be a factor in both the formation of the catalyst-deactivating reaction by-products and also in the formation of other organophosphorus compounds which are derivatives of the ligand whereby, whether these ligand derivatives are themselves catalyst poisons or not, their formation causes an undesired loss of the ligand. Thus, one reason for the unexpectedly benficial results of employing the high stripping rate may be the maintenance within the reaction zone of a reduced concentration of the product aldehyde whereby deleterious reaction sequences involving the aldehyde as an initial reactant are reduced to such a degree that the buildup of high molecular weight catalyst deactivators is no longer appreciable and ceases to be a problem. Because the mechanisms are not known, however, it becomes necessary simply to define the invention in terms of certain stripping parameters, to be explained more fully below, which have been found to be means whereby catalyst deactivation and ligand loss can be very substantially reduced.

Related to the foregoing matter of ligand loss although not, directly at least, a factor in catalyst deactivation, is the loss of ligand through formation of relatively volatile alkyl-substituted derivatives of the ligand in which one or more of the organic substituents of the original ligand is replaced by a substitutent alkyl moiety derived from the olefin reactant. That is, taking the hydroformylation of propylene in a system comprising triphenylphosphine as an example, there is normally a substantial, and undesired, loss of triphenylphosphine through conversion to the relatively volatile propyldiphenylphosphine. This phenomenon is not believed to be directly related to the catalyst deactivation problem, although it does indicate that the triphenylphosphine is not chemically inert in the reaction system (as is also indicated, of course, by the fact that high molecular weight organophosphorus compounds are also formed).

It is to be understood that the present process improvement does not lie in the discovery of undesirable reaction effects that are due to the presence of any single chemical species in the reaction zone. Rather, it lies in the discovery that, regardless of the identity of the particular olefinic reactant being employed and regardless of the identity of the specific triorganophosphorus ligand, there are reaction by-products in rhodium-catalyzed hydroformylation reactions employing olefins and triorganophosphorus ligands, the presence of which by-products leads to catalyst deactivation and ligand consumption unless steps are taken to retard the reactions leading to formation of catalyst deactivating end products.

The following is set forth by way or more specific explanation of the reaction environment within which the present process improvement has specific applicability:

The olefinic reactant employed in the hydroformylation process is one which has an ethylenic double bond in the alpha position in the molecule. Polyunsaturated molecules can be employed, with double bonds in positions other than at the ends of the molecule not necessarily taking part in the hydrocarbonylation reaction. In terms of commercial importance, alpha-alkenes having from two to about twenty carbon atoms are most often employed. Alkenes of three to about ten carbon atoms are especially important industrially. The olefinic reactants may be either straight-chain or branched-chain and, as recognized in the existing art, may contain substituent groups if said substituent groups do not interfere with the course of the hydroformylation reaction. For example, as already reported in the literature, such substituents as carbonyl, oxy, hydroxy, carboxy, halo, alkoxy, phenyl, haloalkyl, etc. can be employed. In addition to the simple alkenes which, as already indicated, are of major industrial significance in the process, the olefinic reactant employed can also be, for example, an aromatic-substituted alkene such as styrene or 3-phenyl-1-propene; dialkenes such as 1,4-hexadiene or 1,7-octadiene; alicyclic-substituted alkenes such as 3-cyclohexyl-1-butene; unsaturated alcohols such as allyl alcohol; unsaturated esters such as allyl acetate and vinyl propionate as well as the alkyl esters of methacrylic acid; unsaturated ethers such as vinylethyl ether and allylethyl ether; and the like. Of the foregoing, alpha-olefinic compounds which are free of substitutent moieties other than hydrocarbyl groups and those containing only carbon, hydrogen, and oxygen in the molecule are preferred.

The ligands employed are most suitably selected from the group consisting of triarylphosphines, triarylphosphites, and triarylphosphites, with the triarylphosphines and triarylphosphites being normally most suitable. Also applicable and embraced within the scope of the present invention are complex ligands comprising triorganophosphines partially substituted with ferrocene, as disclosed in U.S. patent application Ser. No. 650,405 filed by J. D. Unruh et al. on Jan. 19, 1976, Broadly, however, any triorganophosphorus ligand known to the art as being suitable in the rhodium-catalyzed hydroformylation reaction systems is subject to the undesired deterioration reactions which have been found to take place in the absence of the intensive reaction stripping the employment of which is central to the present process improvement. As a practical matter, however, triphenylphosphine is a specific ligand which is widely used industrially and which is subject to the deterioration process which are ameliorated by employment of the present process improvement.

The method by which the catalytic complex of rhodium with the triorganophosphorus ligand and carbon monoxide is introduced into the hydroformylation reaction system is of no consequence insofar as applicability of the present improvement is concerned. That is, once the catalytic complex is present in the reaction medium, its introduction having been carried out according to any of several alternatives well known to the art, its deactivation at a greater or a lesser rate has been found to take place in the absence of the present improvement. It will be understood that the ratio of ligand to rhodium in the catalyst complex can vary over a wide range, but normally the liquid reaction medium contains at least about one mole of triorganophosphorus compound (e.g. triphenylphosphine) per atom of rhodium. Typically the liquid reaction medium will contain about 0.01 to 1.0 weight percent rhodium although the catalyst-deactivation phenomena with which the present process is concerned take place regardless of the rhodium concentration.

The ratio of hydrogen to carbon monoxide in the gases which are introduced into the reaction zone in the hydroformylation process can vary over a wide range as already known to the art. However, a molar ratio of hydrogen to carbon monoxide of about 0.5:1 to 10:1 is normally employed. Likewise the partial pressure of hydrogen and carbon monoxide employed in the reaction can vary widely, but as a practical matter the industrial applications of the process are normally carried out under a total combined partial pressure of hydrogen and carbon monoxide which is within the range of about 4 to 20 atmospheres.

The hydroformylation reaction temperature is normally within the range of about 80° C. to 150° C., with a temperature of about 100° C. to 130° C. being frequently preferred and of particular industrial utility.

The liquid reaction medium can be either a mixture of liquids which are inherently present (i.e., reaction products, excess ligand, etc.) or it may optionally also comprise a separately-added solvent species which is inert under the reaction conditions and in which the catalyst and the excess ligand are soluble. When no separate solvent species is employed, the reaction medium most commonly comprises excess ligand (e.g., triphenylphosphine) and reaction products, including especially those by-products which are less volatile than the carbonyl reaction product itself.

When the reaction is carried out in the presence of a separately-added solvent species, it is well known in the art to employ any of a large number of inert liquids including, for example, alkyl-substituted benzenes; pyridine and alkyl-substituted pyridines; tertiary amines; high-boiling esters such as dialkyl dicarboxylates and triorganophosphates as well as esters of polyols such as trimethylolpropane and pentaerythritol; ketones; alcohols such as the butanols; nitriles such as acetonitrile; and hydrocarbons including both saturated hydrocarbons such as kerosene, mineral oil, cyclohexane, naphtha, etc. as well as the aromatic hydrocarbons already mentioned. In addition to these art-recognized solvents, however, it has now been discovered, in conjunction with the present employment of reaction stripping which is higher than that normally employed in the prior art, that it is desirable to employ solvent species which are of extremely low volatility, in particular compounds (or mixtures of compounds) which are less volatile than the ligand species being employed in the hydrocarbonylation reaction. Particularly useful solvents in this category include triphenylphosphine oxide (which has a relatively high melting point but which is employed in the reaction zone in mixtures which are liquid at the reaction temperature) and polyglycols (e.g., polyethylene glycol and polypropylene glycol) which have molecular weights of at least about 500. High-boiling esters of vapor pressure lower than that of the ligand being employed are also useful, either alone or in admixture with another solvent species, e.g., the polyglycol. The use of such high-boiling solvents facilitates use of the intense stripping characteristic of the present process improvement and, in addition, facilitates maintaining in the reaction liquid a concentration of excess ligand (e.g., triphenylphosphine) which is lower than that which would be present if the ligand were itself the major component of the liquid reaction medium. Ligand concentration is known to affect catalyst activity, the higher ligand concentrations being associated with lower catalyst activity although with a concomitant increase in reaction selectivity. While a wide range of ligand concentration can be employed, 50 wt% or less is often employed, in the case of triphenylphosphine ligand, to maintain a reasonable balance between rate and selectivity. In reaction systems in which the present high stripping is not employed, the higher molecular weight reaction by-products can themselves constitute a major portion of the reaction medium, as in the German Offenlegungsschrift No. 2062703 mentioned hereinabove, whereby the undersirable effects of an overly-high ligand concentration are not experienced. However, when adopting the present high stripping it may become desirable to employ a separately-added high-boiling solvent species. Many such solvents will suggest themselves to one skilled in the art, the requirements being, as mentioned above, chemical inertness in the hydroformylation reaction system, a boiling point higher than, or at least as high as, that of the aldol-type reaction by-products, the ability to act as a solvent for the catalytic complex, and miscibility with, or at least the ability to dissolve substantial quantities of, the olefinic reactant.

Of particular importance in the present improved process as distinguished from the prior art are the high-boiling organophosphorus reaction by-products which are present in the liquid reaction medium and which, in accordance with the present invention, are closely controlled as to concentration. More generally, what is actually controlled is not the concentration of these organophosphorus high boilers per se but, rather, the ratio of the organophosphorus high boilers, as conveniently expressed in terms of their phosphorus content, to the triorganophosphorus ligand which is present, as measured by its phosphorus content. To recapitulate, the present invention in its broadest aspects lies in continuously stripping the liquid reaction medium contained in the hydroformylation reaction zone to such a degree that the ratio of phosphorus contained in organophosphorus high boilers to phosphorus contained in the ligand which is present in the reaction zone does not exceed about 0.2. As previously explained, the exact chemical nature of these organophosphorus high boilers is not known, but for present purposes they can be empirically defined as being those phosphorus-containing organic reaction by-products which are less volatile than the triorganophosphorus ligand being employed, with the oxide of the triorganophosphorus ligand not being included as part of the organophosphorus high boiling by-products in question. That is, the oxides of the ligands in question are formed by a separate mechanism not related to the degree of stripping, such that the degree of stripping does not affect their formation rate. Also, these oxides have no deleterious effect on catalyst activity and they are, for present purposes, inerts. Also not included among the high-boiling organophosphorus compounds which are controlled in accordance with the present process are the alkyl-substituted derivatives of the ligands which are formed by reaction between the ligands and the olefinic reactant, i.e., propyldiphenylphosphine which is formed to some extent in the course of reacting propylene in the presence of triphenylphosphine. Like the ligand oxides, these alkyl-substituted derivatives have no adverse effect on the catalyst activity and their presence is not correlatable with catalyst deactivation.

Without knowing the exact chemical composition of the organophosphorus high-boilers it is nevertheless possible for present purposes for one of normal skill in analytical chemistry to determine their concentration as follows: first, chromatographic methods well known in the art are employed in conventional manner to determine the concentration of identifiable phosphorus compounds known to be present in a normally-operating reaction system. These are, specifically, the ligand which is being employed, the alkyl-substituted derivative formed by reaction of the ligand with the olefinic reactant present in the system, the oxides of the ligand and of its alkyl-substituted derivative, and any other phosphorus compound which may be present as a separately-added solvent species (e.g., a phosphorus ester such as tricresylphosphate). The phosphorus contained in these components of the system can then be readily calculated in terms of weight percent phosphorus present in the form of these named compounds. Next, the total phosphorus in the system, from whatever source, is determined by an oxidative digestion of a sample of the reaction medium (as with a mixture of nitric acid, perchloric acid, and water) followed by a simple chemical analysis for the resulting phosphate ions by conventional methods, such as colorimetry. One has thus determined (a) the total phosphorus content of the reaction medium, (b) the total phosphorus present as ligand, and (c) the total phosphorus present in the above-described identifiable forms other than (b). The phosphorus which is present as the high-boiling organophosphorus reaction by-products is (a) less the sum of (b) and (c). The present invention lies in continuously stripping the reaction medium to such a degree that [(a)−(b+c)] divided by (b), the "control ratio", does not exceed about 0.2. Preferably it does not exceed about 0.05. Most preferably it is kept at a level not exceeding detectable limits, operation at essentially "zero" level being in fact feasible and preferred.

In the matter of the high-boiling organic by-products it is to be emphasized that the present process improvement resides not so much in stripping these from the reaction system once they have already been formed but, rather, in the discovery that they do not build up at all, beyond a certain initial amount which is not unacceptably deleterious, if one maintains continuously a degree of reaction stripping above a certain level. That is, the concentration of these high boilers in relation to that of the ligand is used as a process control index which can be continuously observed and used in setting the stripping rate. If the stripping rate is set sufficiently high, using this index, the further formation of the high boilers (above an initial amount in which a nominal quantity can be allowed to form in the course of setting a base line for the stripping rate) does not take place.

In carrying out the present hydroformylation reactions a conventional method already employed in the existing art is as follows:

The liquid reaction medium containing the rhodium complex catalyst along with, typically, an excess of the organophosphorus ligand and a suitable inert solvent, is contained in a reaction zone maintained under controlled conditions of temperature and pressure. A mixture of hydrogen, carbon monoxide, and the olefinic reactant (with the olefin being initially in either liquid or vapor form as may be convenient) is continuously introduced below the surface of the liquid contained in the reaction zone, within which the catalytic hydroformylation reaction takes place. The mixture being fed into the reaction zone may also frequently contain inerts, such as methane, nitrogen, and the saturated derivative of the olefin, these inerts being present as a result of their having been accumulated in the course of recycling unreacted materials back to the reactor inlet as will be explained below.

When the olefin and its carbonylated derivative are relatively volatile, as is the case in the hydroformylation of propylene, the aldehyde product is evolved from the surface of the liquid contained in the reaction zone as a result of being stripped therefrom by the bubbles of gaseous inerts, unreacted hydrogen and carbon monoxide, as well as unreacted propylene, which evolve from the surface of the liquid reaction medium to be subsequently withdrawn from the reaction zone to be partially condensed to form a liquid product containing the aldehyde and an uncondensed vapor containing unreacted hydrogen, carbon monoxide, propylene, inerts, etc. which is normally recycled to the reaction zone as mentioned above. Ultimate disposition of the crude condensed reaction product is outside the scope of the present invention, but it consists of a product workup by entirely conventional methods, such as distillation, to recover the product carbonyl compounds.

When the olefin is of relatively high molecular weight, e.g., when it contains approximately four carbon atoms or more, the hydroformylated derivative tends to build up in the reaction zone to such an extent that it begins to constitute an undesirably large portion of the reaction medium. In these cases of relatively low-volatility products it is desirable to continuously withdraw a slip stream of liquid from the reaction zone and to distill the product carbonyl compound therefrom at a rate such as to control the buildup of heavy ends, both organophosphorus compounds and phosphorus-free heavy ends. Alternatively, it is possible to supply heat to the reaction zone itself at such a level as to boil out the product carbonyl compound, a rectification column being employed then to rectify the evolved vapors and return into the reaction zone those components, such as the ligand, which it is desired not to remove.

Whichever of the approaches summarized above is employed, the practice of the prior art has been to allow a relatively high carbonyl concentration in the reaction zone and to take high-boiler formation as being an inherent aspect of the process. All the prior art has done heretofore with regard to the high boilers is to suggest the removal of a specific fraction (i.e., the unsaturated aldehydes) as, for example, a distillation cut, with the remaining high boilers being returned to the reaction zone as beneficial solvents.

In carrying out the present process improvement, the hydroformylation reaction can be carried out in very much the same manner as in the above-described prior art methods with the exception that the rate at which the gases are recirculated through the reaction zone or, alternatively, the degree to which the reaction medium is stripped in a separate slip-stream distillation if one is employed, is increased sufficiently that the concentration of the high-boilers as defined hereinabove is not allowed to rise above the level at which the phosphorus contained in the organophosphorus high boilers as previously defined does not exceed about 20% of the amount of phosphorus present as ligand.

Although some specific embodiments of the invention will be explained below in quantitative terms as regards recycle rates etc., it will be seen that it is not feasible to define it in terms of specific numerical stripping ratios but, rather, that it is best defined in terms of the maintenance of a set limit on the ratio of organophosphorus high-boilers to ligand in the reaction medium, as explained above, with the stripping ratio (the ratio of the quantity of gas passed through the reaction zone to the quantity of liquid contained therein) being simply a dependent variable. This is for the reason that the stripping ratio required in a given situation will be different from that required in another because of differences in such factors as reaction temperature; gas composition; reaction zone configuration; hydroformylation catalyst composition, concentration, and condition, etc. In all cases, however, the presently-recommended stripping rate will be found to be substantially in excess of that which would be suggested by the prior art when the only purpose is to maintain the steady state concentration of carbonyl reaction products and unsaturated aldehydes which have hitherto been maintained in the reaction zone.

The following examples are given to illustrate the invention further in comparison with prior-art technology. It will be recognized that many variations can be made within the scope of the invention.

EXAMPLE I

Propylene, carbon monoxide, and hydrogen were introduced continuously beneath the surface of a liquid reaction medium contained in a vessel maintained at a temperature of about 115° C. and at a pressure of about 20 atmospheres absolute. Unreacted gases evolving from the surface of the liquid reaction medium were drawn off from the top of the reaction vessel and passed through a condenser operated at about 50° C. to produce a product consisting of condesned liquid and non-condensable gases. Both the gases and the liquid product were measured and analyzed chemically.

Per unit volume of liquid contained in the reaction zone the continuously-introduced gases amounted to approximately 150 unit volumes per hour measured at operating temperature and pressure. The gases as introduced comprised, by volume, 35% hydrogen, 15% carbon monoxide, 20% propylene, and the remainder inert gases. The liquid reaction medium contained in the reaction zone comprised by weight, under steady-state operating conditions, approximately 30% butyraldehyde, 32% total heavy-ends reaction by-products of all types, 3% propyldiphenylphosphine, 32% triphenylphosphine (including both triphenylphosphine which was complexed with the rhodium hydrocarbonylation catalyst and that which was present in an amount in excess of that required for complexation), and 3% triphenylphosphine oxide. Active rhodium, in the form of a complex with triphenylphosphine and carbon monoxide, was present in a concentration of 0.12 wt% computed as the metal.

Phosphorus present as triphenylphosphine amounted to 3.8 wt% of the reaction medium, calculated as phosphorus. Phosphorus present in the form of high-boiling organophosphorus by-products as previously defined amounted to 2.4 wt% of the reaction medium, also calculated as phosphorus. The "control ratio" as defined hereinabove was 0.6. Operating as described above, the reaction system produced butyraldehyde at an initial rate of approximately 500 grams per hour per liter of liquid reaction medium, but a continuing decline in catalyst activity, as indicated by a continuing increase in the concentration of unreacted propylene in the gases evolved from the reaction zone, necessitated increasing the rhodium concentration to 0.24 wt% over a period of 100 days to maintain the initial reactor productivity. The concentration of unsaturated aldehyde reaction by-product in the liquid reaction medium during this period was very low, i.e., of the order of 0.3 wt%, whereby, insofar as the prior art is concerned, deactivation from this source would not have been expected.

EXAMPLE II

In a reaction system operating substantially as described in Example I but under conditions of high stripping, attained by increasing the through-put of gases through the reaction zone, operating conditions were as follows:

Temperature and pressure in the reaction zone were approximately 115° C. and 20 atmoshperes absolute, respectively. The mixture of hydrogen, carbon monoxide, propylene, and inert gases was introduced into the liquid reaction medium at a rate of 400 volumes per hour, measured at operating temperature and pressure, per unit volume of reaction medium contained in the reaction zone. These introduced gases comprised, by volume, approximately 35% hydrogen, 15% carbon monoxide, and 20% propylene.

Operating as described above, the liquid contained in the reaction zone comprised, by weight, approximately 14% butyraldehyde, 1% high-boiling reaction by-products, 2% propyldiphenylphosphine, 40% total triphenylphosphine, and 0.25 wt% rhodium calculated as the metal. The unsaturated aldehyde heavy ends amounted to less than 0.1 wt%. The liquid reaction medium also contained 43 wt% of polyethylene glycol, employed as an inert reaction solvent. Phosphorus present as organophosphorus high-boilers as previously defined was below the limits of detectability. Within the limits of analytical accuracy, the "control ratio" as defined hereinabove was zero.

Operating as above, the reaction system produced, per liter of liquid reaction medium contained in the reaction zone, approximately 1000 grams of butyraldehyde per hour per liter of liquid reaction medium, and no increase in catalyst concentration was necessary to maintain this level of reactor productivity during 50 days of operation.

EXAMPLE III

In the hydrocarbonylation of 1-octene there was employed a reaction system which comprised a reaction zone containing a liquid reaction medium and also comprising a distillation column to which there was continuously fed a liquid slip stream continuously withdrawn from the reaction zone at a rate of about 2.5 unit volumes per hour per unit volume of liquid in the reaction zone. A gas comprising 45% hydrogen, 45% monoxide, and 10% inert gases including methane and nitrogen was continuously circulated through the reaction zone, and then through a condenser, from which condenser the liquid condensate formed therein was returned to the reaction zone. Gas exiting from the condenser was also returned back to the reaction zone. The reaction zone was maintained at a temperature of about 105° C. and at a pressure of about 10 atmospheres absolute. The gases recirculated through the reaction zone amounted to about 250 volumes per hour, measured at operating temperature and pressure, per volume of liquid contained in the reaction zone. The 1-octene was continuously introduced into the reaction zone, in liquid form, at a rate of about 0.5 volumes of liquid per volume of liquid contained in the reaction zone, per hour.

Volatile liquids (i.e., crude reaction product comprising $C_9$ aldehydes) were continuously distilled, at about 8 mmHg absolute pressure and at a stripper column base temperature of about 115° C., with the stripped residue being returned to the hydrocarbonylation reaction zone. The overhead product from the distillation column was measured and analyzed chemically in order to continuously monitor the progress of the hydrocarbonylation reaction. The stripped residue returned from the distillation column to the reaction zone contained approximately 5 wt% $C_9$ aldehydes.

During the course of the reaction the liquid carbonylation reaction medium contained in the reaction zone comprised, under steady-state reaction conditions, about 40 wt% $C_9$ aldehydes, 10 wt% high-boiling reaction by-products, 45 wt% triphenylphosphine, 5 wt% triphenylphenylphosphine oxide, and 0.25 wt% rhodium calculated as the metal. The phosphorus which was present in the form of organophosphorus high boilers as previously defined hereinbelow was undetectable. The "control ratio" was zero within the limits of analytical accuracy.

The unsaturated aldehyde by-product of the type previously taught in the art as being deleterious to catalyst activity was present in the reaction medium in a concentration of about 3 wt%.

The steady-state production of $C_9$ aldehydes from the system operating as described above was approximately 1000 grams of $C_9$ aldehydes per hour per liter of contained liquid reaction medium, and this production rate was maintained, without the need for increasing the rhodium concentration, over a period of about 60 days.

It is to be noted that the catalyst activity did not decline under these conditions even though the unsaturated aldehyde by-product content was comparatively high, indicating that the presence of this material at this relatively high concentration was not noticeably deleterious and was not a significant factor affecting catalyst activity.

It will be seen that, in this Example the stripping of the liquid reaction medium is accomplished by simple distillation, rather than by the gas stripping used in Examples I and II. The term "stripping" is employed in the present specification in its broader sense; that is, the term is intended to embrace all operations for transferring material from the liquid to the vapor phase including gas stripping, distillation, and simple evaporation.

The embodiments of the invention in which an exclusive property or privilege is claimed are defined as follows:

1. In a process for hydroformylating a hydrocarbon of 2 to about 20 carbon atoms having an ethylenic double bond in the alpha position by reacting said hydrocarbon at about 80° C. to 150° C. with carbon monoxide and hydrogen in admixture with a liquid reaction medium containing as hydroformylation catalyst a complex of rhodium with a triorganophosphorus ligand and carbon monoxide to produce a liquid reaction product comprising said ligand, an aldehyde derivative of said hydrocarbon, and reaction by-products, the improvement which comprises:

continuously stripping said liquid reaction medium, by gas stripping, distillation, or evaporation during the course of said hydroformylation reaction, to such a degree that the ratio of (a) phosphorus contained in said liquid reaction medium in the form of high-boiling organophosphorus reaction by-products excluding alkyl-substituted derivatives of said ligand formed by substitution of said olefin into said ligand molecule and also excluding oxides of said ligand and of said alkyl-substituted derivatives to (b) phosphorus contained in said reaction medium in the form of said ligand is maintained at a value not greater than about 0.2.

2. The improvement of claim 1 wherein the triorganophosphorus ligand is triphenylphosphine and wherein said liquid reaction medium contains at least about one mole of triphenylphosphine per atom of rhodium.

3. The improvement of claim 2 wherein said liquid reaction medium comprises an inert liquid which is less volatile than triphenylphosphine.

4. The improvement of claim 2 wherein said alpha-olefinic hydrocarbon is an alkene having from 2 to about 20 carbon atoms.

5. The improvement of claim 4 wherein the alkene has from 3 to about 10 carbon atoms.

6. The improvement of claim 5 wherein said hydroformylation reaction is conducted and under a partial pressure of about 4 to 20 atmospheres of hydrogen and carbon monoxide combined, the molar ratio of hydrogen to carbon monoxide being about 0.5:1 to 10:1.

7. The improvement of claim 6 wherein the liquid reaction medium contains about 0.01 to 1.0% rhodium by weight and about 20 to 80% triphenylphosphine by weight.

8. In a process for hydroformylating a hydrocarbon of 2 to about 20 carbon atoms having an ethylenic double bond in the alpha position by reacting said hydrocarbon at about 80° C. to 150° C. with carbon monoxide and hydrogen in admixture with a liquid reaction medium containing as hydroformylation catalyst a complex of rhodium with a triorganophosphorus ligand and carbon monoxide to produce a liquid reaction product comprising said ligand, an aldehyde derivative of said hydrocarbon, and reaction by-products, the improvement which comprises:

continuously stripping said liquid reaction medium during the course of said hydroformylation reaction, by passing a gas comprising said hydrogen and carbon monoxide therethrough, to such a degree that the ratio of (a) phosphorous contained in said liquid reaction medium in the form of high-boiling organophosphorus reaction by-products excluding alkyl-substituted derivatives of said ligand formed by substitution of said olefin into said ligand molecule and also excluding oxides of said ligand and of said alkyl-substituted derivatives to (b) phosphorus contained in said reaction medium in the form of said ligand is maintained at a value not greater than about 0.2.

9. The improvement of claim 8 wherein said hydrocarbon is an alkene having from 3 to about 10 carbon atoms.

10. In a process for hydroformylating a hydrocarbon of 2 to about 20 carbon atoms having an ethylenic double bond in the alpha position by reacting said hydrocarbon at about 80° C. to 150° C. with carbon monoxide and hydrogen in admixture with a liquid reaction medium containing as hydroformylation catalyst a complex of rhodium with a triorganophosphorus ligand and carbon monoxide to produce a liquid reaction product comprising said ligand, aldehyde derivative of said hydrocarbon, and reaction by-products, the improvement which comprises:

continuously stripping said liquid reaction medium during the course of said hydroformylation reaction, by continuously distilling vapors comprising said aldehyde derivative out of said liquid reaction medium, to such a degree that the ratio of (a) phosphorus contained in said liquid reaction medium in the form of high-boiling organophosphorus reaction by-products excluding alkyl-substituted derivatives of said ligand formed by substitution of said olefin into said ligand molecule and also excluding oxides of said ligand and of said alkyl-substituted derivatives to (b) phosphorus contained in said reaction medium in the form of said ligand is maintained at a value not greater than about 0.2.

11. The improvement of claim 10 wherein said hydrocarbon is an alkene having from 3 to about 10 carbon atoms.

* * * * *